United States Patent
Etheridge et al.

(10) Patent No.: US 8,906,827 B2
(45) Date of Patent: *Dec. 9, 2014

(54) COMPOSITIONS AND METHODS FOR RESIDUAL WEED CONTROL WITH FLUMIOXAZIN AND GIBBERELLIC ACID

(71) Applicant: Valent U.S.A. Corporation, Walnut Creek, CA (US)

(72) Inventors: Jimmy R. Etheridge, Walnut Creek, CA (US); John Andrew Pawlak, II, Walnut Creek, CA (US)

(73) Assignee: Valent U.S.A., Corporation, Walnut Creek, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/069,616

(22) Filed: Nov. 1, 2013

(65) Prior Publication Data

US 2014/0128261 A1 May 8, 2014

Related U.S. Application Data

(60) Provisional application No. 61/722,466, filed on Nov. 5, 2012.

(51) Int. Cl.
*A01N 43/40* (2006.01)
*A01N 43/84* (2006.01)
*A01N 43/08* (2006.01)

(52) U.S. Cl.
CPC ............... *A01N 43/08* (2013.01); *A01N 43/84* (2013.01)
USPC ........................................................ 504/130

(58) Field of Classification Search
None
See application file for complete search history.

(56) References Cited

U.S. PATENT DOCUMENTS 4,154,596 A 5/1979 George et al.
2008/0305952 A1 12/2008 Arnevik et al.

OTHER PUBLICATIONS

Whitaker et al., "Residual Herbicides for Palmer Amaranth Control." The Journal of Cotton Science, 2011, vol. 15, pp. 89-99.
Valent Valor SX Herbicide 2010.
Valent BioSciences Berelex 40 SG Plant Growth Regulator Mar. 2009.

*Primary Examiner* — Alton Pryor
(74) *Attorney, Agent, or Firm* — Wood, Phillips, Katz, Clark & Mortimer

(57) ABSTRACT

The invention relates to compositions and methods for controlling amaranth by application of flumioxazin and gibberellic acid to an area in need of weed control.

17 Claims, 2 Drawing Sheets

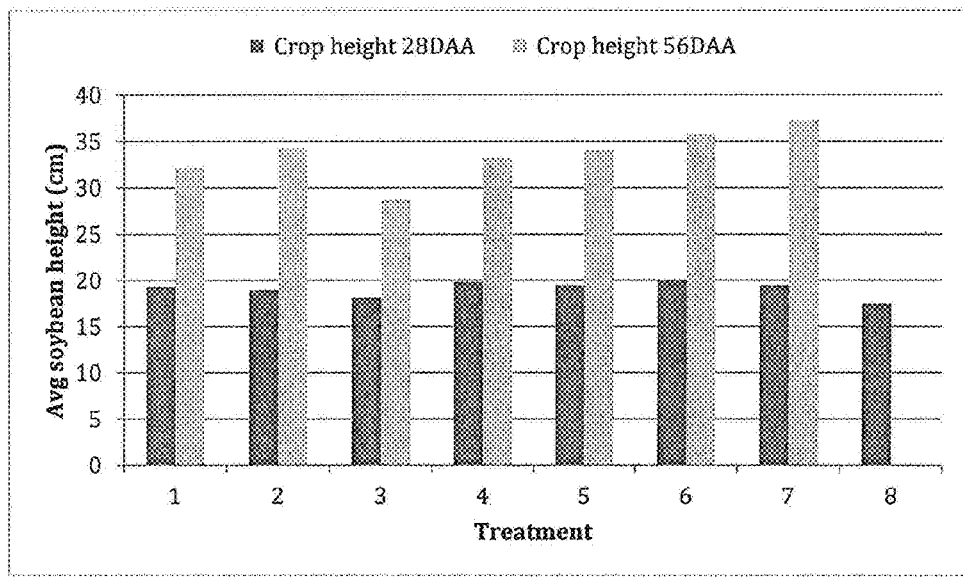
Figure 1. Average soybean height (in cm) at Ferré, 28 and 56 days after treatment application.
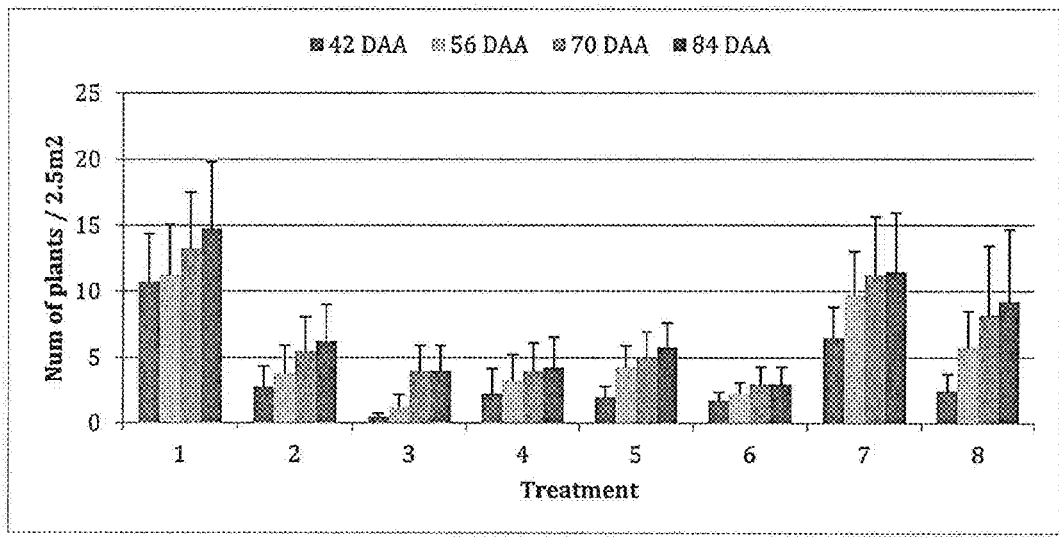
Figure 2. Number of seedlings and plants of *Amaranthus quitensis* at Acevedo at 42, 56, 70 and 84 days after treatment application.

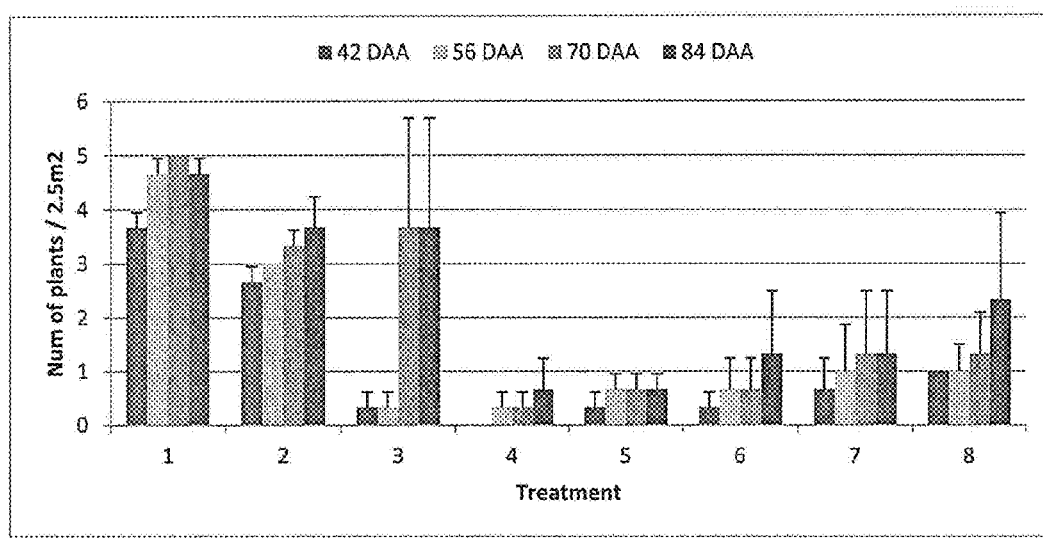
Figure 3. Number of seedlings and plants of *Amaranthus quitensis* at Ferré at 42, 56, 70 and 84 days after treatment application.

US 8,906,827 B2

COMPOSITIONS AND METHODS FOR RESIDUAL WEED CONTROL WITH FLUMIOXAZIN AND GIBBERELLIC ACID

FIELD OF THE INVENTION

The present invention is directed to compositions and methods for protecting crop plants from weeds with a combination of flumioxazin and gibberellic acid.

BACKGROUND OF THE INVENTION

The present compositions and methods are directed to applying effective amounts of flumioxazin and gibberellic acid to an area in need of weed control.

One of the major concerns of crop plant growers is the presence of undesired plants, such as weeds, in the area where the crop plant is grown. Weeds contribute to decreased crop yields because the crop plants must compete with weeds for limited available resources such as sunlight, soil nutrients, and water. Weeds can also host pests that can increase disease rates in crop plants.

One weed in particular, Palmer amaranth, *Amaranthus palmeri*, is an aggressive grower and prolific seed producer and accordingly is a threat to crop plants. It can quickly outgrow and dominate many crop plants if not carefully controlled. Recently, Palmer amaranth has shown resistance to the common herbicide glyphosate. If a grower finds that the Palmer amaranth is glyphosate resistant, the grower has little hope of controlling an infestation. There are no chemicals that will control large, glyphosate resistant Palmer amaranth that emerge late in the season.

Therefore, there is a need in the art for a highly effective and safe residual weed control method, especially for the treatment of Palmer amaranth and other amaranth weeds such as waterhemp (*Amaranthus rudis*) and *Amaranthus quitensis*.

SUMMARY OF THE INVENTION

Applicants have discovered that a combination of flumioxazin and gibberellic acid provides excellent residual weed control.

In one aspect, the invention is directed to methods of pre-emergent weed control comprising applying an effective amount of flumioxazin and an effective amount of gibberellic acid to an area in need of weed control.

In another aspect, the area in need of weed control is an area used for crop plant growth. Applicants' methods can be applied to areas growing a variety of crop plants and is effective on hard-to-kill weeds.

BRIEF DESCRIPTION OF THE DRAWINGS

FIG. 1. Average Soybean Height in cm at Ferre, 28 and 56 days after treatment application shows the average crop height for each treatment as explained in Example 2.

FIG. 2. Number of Seedling and plants of *Amaranthus quitensis* at Acevedo at 42, 56, 70 and 84 days after treatment application shows the average number of seedlings present in each treated plot as explained in Example 2.

FIG. 3. Number of Seedling and plants of *Amaranthus quitensis* at Ferre at 42, 56, 70 and 84 days after treatment application shows the average number of seedlings present in each treated plot as explained in Example 2.

DETAILED DESCRIPTION OF THE INVENTION

The present invention is directed to compositions and methods for applying flumioxazin and gibberellic acid to an area in need of pre emergent weed control.

Flumioxazin (N-(7-fluoro-3,4-dihydro-3-oxo-4-prop-2-ynyl-2H-1,4-benzoxazin-6-yl)cyclohex-1-ene-1,2-dicarboxamide) is a dicarboximide herbicide. Flumioxazin is an effective pre-emergence herbicide. Valor® (available from Valent U.S.A. Corporation) contains flumioxazin and is known to provide four to six weeks of pre-emergence control of Palmer amaranth.

Gibberellic acid ("$GA_3$") is a plant hormone that promotes growth and elongation of cells. $GA_3$ has no known herbicidal activity, including no known pre-emergence herbicide activity.

Unexpectedly, Applicants found that when $GA_3$ was combined with flumioxazin, $GA_3$ increased the residual activity of the flumioxazin. This was unexpected because $GA_3$ doesn't exhibit any herbicidal activity on its own. Because $GA_3$ is a plant growth regulator that typically improves a plant's growth, one skilled in the art would predict that $GA_3$ would counteract the effects of the flumioxazin and make flumioxazin a less effective herbicide. In contrast, Applicants found that $GA_3$ allowed for a more efficient kill in *Amaranthus palmeri* and *Amaranthus quitensis*.

In one embodiment, Applicants' invention is directed to compositions and methods for controlling weeds before they have emerged which includes applying an effective amount of flumioxazin and an effective amount of $GA_3$ to an area that is anticipated to require weed control.

In another embodiment, the ratio of flumioxazin to $GA_3$ is from about 3.5:1 to about 35:1. More preferably, the ratio is from about 0.187:1 to about 35:1, and the most preferred ratio is about 14:1.

In a further embodiment, the effective amount of flumioxazin is from about 70 to about 105 grams per hectare. More preferably, the effective amount is from about 35 to about 480 grams per hectare, and the most preferred effective amount is about 70 grams per hectare.

In yet another embodiment, the effective amount of $GA_3$ is from about 5 to about 200 grams per hectare. More preferably, the effective amount is from about 5 to about 20 grams per hectare, and most preferred, the effective amount is about 5 grams per hectare.

Applicants' mixtures can be applied by any convenient means. Those skilled in the art are familiar with the modes of application that include pre-emergence applications such as spraying, dusting, and granular application as well as drenching.

In one embodiment, the flumioxazin and $GA_3$ can be applied together as a tank mix and applied simultaneously to an area in need of weed control. Alternatively, the flumioxazin and $GA_3$ can be applied sequentially with either component being applied first.

Applicants' compositions and methods effectively kill weeds in an area that will be planted with crop plants. Applicants' combination of flumioxazin and $GA_3$ can be applied before the weeds and crop plants have germinated and emerged from the ground. The combination can be applied before the crop plants and weeds emerge. The crops may be GMO or non-GMO. As used herein the phrase "GMO crops" is intended to mean crops grown from genetically modified organisms.

In yet another embodiment, Applicants' compositions and methods can be applied successfully to crop plants and weeds that are resistant to glyphosate or other herbicides.

The herbicide combination of the present invention may be formulated to contain adjuvants, such as solvents, anti-caking agents, stabilizers, defoamers, slip agents, humectants, dispersants, wetting agents, thickening agents, emulsifiers, and preservatives which increase the long lasting activity of the actives. Other components that enhance the biological activity of these ingredients may optionally be included.

Mixtures of the present invention can be formulated as a liquid or as a solid. Applicants' mixtures can also include one or more herbicides. Further, the mixtures can include additional ingredients to increase the effectiveness of the active ingredients.

The mixture of the present invention can be applied to any environment in need of weed control. The environment in need of weed control may include any area that is desired to have a reduced number of weeds or to be free of weeds. For example, the mixture can be applied to an area used to grow crop plants, such as a field, orchard, or vineyard. For example, Applicants' methods can be applied to areas where soybeans, corn, peanuts, cotton or other crops/ornamentals will be grown. The weeds may be GMO or non-GMO crops. In a preferred embodiment, the treatment containing the mixture is applied before emergence of the weeds. In another preferred embodiment, the crop plant is soybeans.

The disclosed embodiments are simply exemplary embodiments of the inventive concepts disclosed herein and should not be considered as limiting, unless the claims expressly state otherwise.

As used herein, all numerical values relating to amounts, weight percentages and the like are defined as "about" or "approximately" each particular value, namely, plus or minus 10% (±10%). For example, the phrase "at least 5% by weight" is to be understood as "at least 4.5% to 5.5% by weight." Therefore, amounts within 10% of the claimed values are encompassed by the scope of the claims.

The term "effective amount" means the amount of the formulation that will kill a weed. The "effective amount" will vary depending on the formulation concentration, the type of plants(s) being treated, the severity of the weed infestation, the result desired, and the life stage of the weeds during treatment, among other factors. Thus, it is not always possible to specify an exact "effective amount." However, an appropriate "effective amount" in any individual case may be determined by one of ordinary skill in the art.

The following examples are intended to illustrate the present invention and to teach one of ordinary skill in the art how to use the formulations of the invention. They are not intended to be limiting in any way.

EXAMPLES

Valor® Herbicide contains 51% flumioxazin and was used throughout the examples as the source of flumioxazin. ProGibb® 4% (available from Valent BioSciences Corporation) contains 4% $GA_3$ and was used in Example 1 as the source of $GA_3$. In Example 2, a 10% $GA_3$ formulation and a 40% $GA_3$ formulation were used.

Example 1

In order to determine the efficacy of combinations of flumioxazin and $GA_3$, treatments were applied to plots that were subsequently planted with Palmer amaranth and incorporated with a triple K and then planted with soybeans.

Crop tolerance and the number of living Palmer amaranth plants were evaluated at 13, 27, 56 and 96 days following the treatment. The results of this study can be found below in "Table 1. Effect of Flumioxazin and $GA_3$ Treatments on Palmer amaranth (% control)."

TABLE 1

Effect of Flumioxazin and $GA_3$ Treatments on Palmer amaranth (% control).

| Trt No | Product | Appl Rate | Rate Unit | Soybean 13 DAT | PA 13 DAT | Soybean 28 DAT | PA 28 DAT | Soybean 56 DAT | PA 56 DAT | Soybean 107 DAT | PA 107 DAT |
|---|---|---|---|---|---|---|---|---|---|---|---|
| 1 | UNTREATED CHECK | | | 0 | 0 | 0 | 0 | 0 | 0 | 0 | 0 |
| 2 | Flumioxazin | 0.063 | lb ai/a | 0.33 | 100 | 0 | 98.67 | 0 | 92 | 0 | 88.33 |
| 3 | Flumioxazin GA3 | 0.063 20 | lb ai/a g ai/a | 0 | 100 | 0 | 99.33 | 0 | 98.3 | 0 | 98.33 |
| 4 | Flumioxazin GA3 | 0.063 200 | lb ai/a g ai/a | 0 | 100 | 0 | 99.67 | 0 | 98.7 | 0 | 96.67 |
| 5 | Flumioxazin GA3 | 0.063 400 | lb ai/a g ai/a | 10 | 100 | 0 | 97.33 | 0 | 87.7 | 0 | 86 |

Applicants unexpectedly found that 107 days after treatment, the mixture of flumioxazin with $GA_3$ provided increased residual control of Palmer amaranth. This study also confirmed that the treatments are not harmful to crop plants, such as soybeans.

Example 2

A further study was completed wherein combinations of flumioxazin and $GA_3$ were applied to areas of *Amaranthus quitensis* infestation. In indicated above, two different concentrations of $GA_3$ formulations were used in this study. This study was designed to determine the impact the combination has on germination when applied in a pre-emergence application.

Two separate trials were completed at Acevedo and Ferre in Argentina. Seeds of *Amaranthus quitensis* were planted by hand-broadcast to the plots. The seeds were collected from natural weeds earlier in the same season. Hand broadcast was used to ensure a homogeneous area of infestation. Immediately following the planting of the *Amaranthus quitensis* seeds, soybeans were planted which also helped incorporate the weed seeds into the soil. A cone planter was used at the Acevedo location and a commercial planter was used at the Ferre location. The experimental design was a completely randomized block with 4 reps at Acevedo and 3 reps at Ferre. The plots were 4 rows in width and 5 meters long. Treatment applications were made prior to emergence of the soybeans with a $CO_2$ backpack sprayer with less than 6 km/h wind speed. The treatments are below in "Table 2. Flumioxazin and $GA_3$ Treatments on Amaranthus quitensis."

TABLE 2

Flumioxazin and GA₃ Treatments on *Amaranthus quitensis*

| Treatment | Actives | Rate | Units |
|---|---|---|---|
| 1 | Untreated check | n/a | n/a |
| 2 | 51% flumioxazin | 70 | gmai/ha |
| 3 | 51% flumioxazin<br>40% GA₃ | 70<br>12.5 | gmai/ha |
| 4 | 51% flumioxazin<br>40% GA₃ | 70<br>25 | gmai/ha |
| 5 | 51% flumioxazin<br>40% GA₃ | 70<br>50 | gmai/ha |
| 6 | 51% flumioxazin<br>10% GA₃ | 70<br>12.5 | gmai/ha |
| 7 | 51% flumioxazin<br>10% GA₃ | 70<br>25 | gmai/ha |
| 8 | 51% flumioxazin<br>10% GA₃ | 70<br>50 | gmai/ha |

Crop tolerance/phytotoxicity was measured 14, 28, and 56 days after the application. Unfortunately, the Acevedo location suffered hail damage and the phytotoxity of the crop could not be determined. At the Ferre location, crop height was measured as an indication of phytotoxicity (see FIG. 1).

Efficacy of the treatment was measured by counting the number of Amaranthus at 42, 56, 70 and 84 days after the application. The Amaranthus plants were counted between two rows at the center of the plot (total area 2.5 square meters). The phytotoxicity of Amaranthus was also evaluated (see FIGS. 2 and 3).

Data was analyzed with Infostat to determine the significance of the data. An alpha level of 0.1 was used for mean comparisons.

Applicants found that soybeans did not exhibit any phytotoxicity to the combination treatments. See "FIG. 1. Average Soybean Height in cm at Ferre, 28 and 56 days after treatment application."

Applicants found that the treatments were very effective at controlling *Amaranthus quitensis*. See "FIG. 2. Number of Seedling and plants of *Amaranthus quitensis* at Acevedo at 42, 56, 70 and 84 days after treatment application." See also "FIG. 3. Number of Seedling and plants of *Amaranthus quitensis* at Ferre at 42, 56, 70 and 84 days after treatment application." The bars represent one standard error of the mean.

The inventiom claimed is:

1. An agricultural composition comprising a mixture of an effective amount of flumioxazin and an effective amount of gibberellic acid (GA₃), wherein the flumioxazin and GA₃ together povides improved weed control over flumioxazin or GA₃ applied alone.

2. The composition of claim 1 wherein the flumioxazin and GA₃ are in a ratio range of from about 1:0.175 to about 1:35.

3. The composition of claim 2 wherein the flumioxazin and GA₃ are in a ratio of about 3.5:1.

4. A method for amaranth control comprising applying an effective amount of flumioxazin and an effective amount of gibberellic acid (GA₃) to an area in need of amaranth control, wherein the flumioxazin and GA₃ together provides improved amaranth control over flumioxazin or GA₃ applied alone.

5. The method of claim 4 wherein the flumioxazin and GA₃ are in a ratio range of from about 1:0.175 to about 1:35.

6. The method of claim 5 wherein the flumioxazin and GA₃ are in a ratio of about 3.5:1.

7. The method of claim 4 wherein the effective amount of GA₃ is from about 20 to about 200 grams per acre.

8. The method of claim 4 wherein the flumioxazin and GA₃ are applied by spraying, or granular application.

9. The method of claim 4 wherein the flumioxazin and GA₃ are applied simultaneously or sequentially.

10. The method of claim 4 wherein the amaranth is *Amaranthus palmeri*.

11. The method of claim 4 wherein the amaranth is *Amaranthus quitensis*.

12. A method for providing residual amaranth control in an area to be planted with crop plants comprising: (a) applying an effective amount of flumioxazin to the area; (b) applying an effective amount of GA₃ to the area; and (c) planting crop plants in the area, wherein the flumioxazin and GA₃ together provides improved residual amaranth control over flumioxazin or GA₃ applied alone.

13. The method of claim 12 wherein the flumioxazin and GA₃ are applied before the crop plants are planted.

14. The method of claim 12 wherein the crop plant is soybean.

15. The method of claim 12 wherein the amaranth is resistant to glyphosate.

16. The method of claim 12 wherein the amaranth the *Amaranthus palmeri*.

17. The method of claim 12 wherein the amaranth is *Amaranthus quitensis*.

* * * * *